Feb. 19, 1963 W. P. THOMSON Plant Pat. 2,227
CARNATION PLANT
Filed April 25, 1962
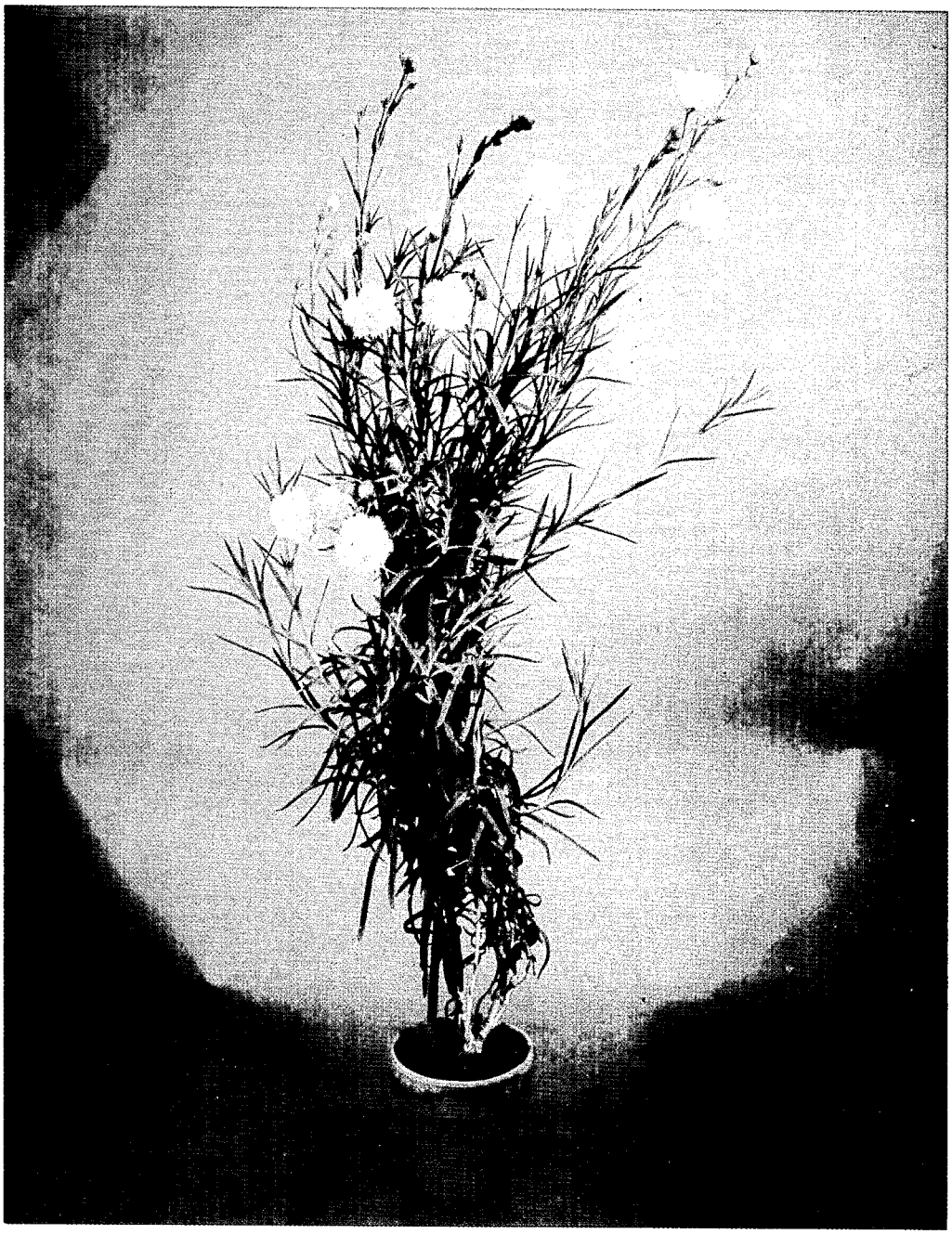
Inventor
W. P. Thomson
by Robb & Robb
attorneys United States Patent Office Plant Pat. 2,227
Patented Feb. 19, 1963

2,227
CARNATION PLANT

William P. Thomson, West Hartford, Conn., assignor to George J. Ball, Inc., West Chicago, Ill., a corporation of Illinois Filed Apr. 25, 1962, Ser. No. 190,187
1 Claim. (Cl. 47—60)

My present invention comprises a new and distinct variety of carnation plant which has been obtained as a result of crossing the variety "Exquisite" an unpatented variety, with another unpatented variety known as "Miller's Yellow."

The object of this invention is a new variety of carnation, *Dianthus caryophyllus,* deriving certain of its characteristics from one parent, and others from the other parent, the combination of which provide a feathery white type having very fragrant flowers.

The characteristics of this particular variety are definite improvements over those of either of the parents.

By careful selection and cross breeding of various plants from various parents, the instant variety has been derived to take advantage of many of the characteristics of both specific parent plants and of the general strain from which the said parent plants have derived, certain of the characteristics desirably being better placing of the flowers on the stem with longer stems for each individual flower and an additional bud on said stem.

In consequence of the specific hybridization previously referred to I have produced my present new and distinct variety of carnation characterized by the very white to very lightly shaded brilliant greenish yellow color of the blooms, the more serrated feathery nature thereof, said blooms being well placed on long graceful stems, with strong fragrance and very vigorous tall plant form.

More specifically the blooms of my new variety are of a very white to very lightly shaded brilliant greenish yellow color (Nickerson Color Fan published by The Munsell Color Company), the blooms having a shading of yellow at the center with the outer edges of the petals being very white and feathery. As grown in the vicinity of West Hartford, Connecticut, in uniform culture, plants of my new variety grow on long stems, each flower having its own stem from 4" to 10" long with an additional bud forming on each flower stem.

My new variety derives a number of characteristics from both parents, but includes better characteristics than either separately, primarily in the more feathery nature of the blooms, the vigorous plant habit with plentiful foliage, the blooms and habit being different from both parents and from other known varieties.

The nearest variety in general to the instant variety is the variety known as "White Elegance," an unpatented variety, but the instant variety grows much taller and has more flowers per stem. The flowers are also more serrated.

My new variety when grown in the vicinity of West Hartford, Connecticut, produces a large number of flowers about 2¼" in diameter, in clusters, continuously.

My new variety has been asexually reproduced, by cuttings taken from the vegetative side growths, in the vicinity of West Hartford, Connecticut.

My new variety has been found to retain its distinctive characteristics through successive asexual reproductions.

The accompanying drawing forming a part hereof shows a typical plant of my new variety of carnation.

The following is a detailed description of my new variety of carnation plant, the color references being to the Nickerson Color Fan published by the Munsell Color Company:

*Description*

Parentage: Seedling.

*Seed parent.*—"Exquisite" (unpatented).
*Pollen parent.*—"Miller's Yellow" (unpatented).

Classification: Botanic—*Dianthus caryophyllus.*

*Flower*

Blooming habit: Blooms profusely and continuously. Observations were made in the vicinity of West Hartford, Connecticut.

Bud:

*Sized.*—Small.
*Form.*—Long and ovoid. It is not affected by wet weather but becomes smaller in hot weather.

Color:

*When sepals first divide.*—White.
*When petals begin to unfurl.*—White.
*When half blown.*—Inside of petals—white. Reverse of petals—white.
*Sepals.*—Serrated.
*Calyx.*—Shape—pear shaped. Size—small and slender. Aspect—smooth.
*Peduncle.* — Length — long. Aspect — smooth. Strength—erect and slender. Buds open well and are affected very little by adverse conditions.

Bloom:

*Size.*—Small. Average size when fully expanded—2¼".
*Borne.*—In clusters, irregularly.
*Stems.*—Long.
*Form.*—When first open—globular. Fashion—like a cactus dahlia.
*Petalage.*—Very double, many petals and stamens hidden. Number of petals—35 under normal conditions.
*Color.*—Center of flower—white, very lightly shaded yellow, somewhere between 7.5Y 9/8 and pure white. Outer petals—white. Base of petals—white shaded green 2.5GY 9/8. Inside of petals—white very lightly shaded yellow 7.5Y 9/8. Reverse of petals—white. General tonality from a distance—white.
*Discoloration.*—General tonality at end of second week—white shaded yellow 5Y 7/10.

Petals:

*Texture.*—Thin and soft. Not affected by wet weather but become smaller in hot weather.
*Appearance.*—Inside—velvety. Outside—velvety.
*Form.*—Scalloped.
*Arrangement.*—Informal.
*Petaloids in center.*—Few and small.
*Persistence.*—Hang on and dry.
*Fragrance.*—Strong, cinnamon spice.
*Lastingness.*—On the plant—long. Cut flower—long.

Genital organs:

*Stamens, anthers.*—Medium, many. Color—white. Arrangement—regular around styles, mixed with petaloids.
*Stamens, filaments.*—Medium length. Color—white.
*Pollen.*—7.5Y 9/8 brilliant greenish yellow.
*Styles.*—Loosely separated. Length—medium.
*Stigmas.*—Color—white.
*Ovaries.*—All enclosed in calyx.

Fruit: Variety is fertile with its own pollen.

*Form.*—Ovoid.
*Aspect.*—Smooth.
*Color at maturity.*—7.5YR 6/9.
*Sepals.*—Permanent, pear shaped.

Plant:

*Form.*—Bush.
*Growth.*—Very vigorous and branching.
*Height.*—Approximately 5 feet at 1 year.

Foliage:

*Leaflets.*—30 per stem.
*Size.*—Medium.
*Quantity.*—Normal.
*Color.*—Upper side—strong bluish green 10G 5/8. Under side—strong bluish green 10G 5/8.
*Shape.*—Lanceolate, long and narrow.
*Texture.*—Upper side—glossy and flat.
*Ribs and veins.*—Light.
*Edge.*—Smooth.
*Under side.*—Smooth.

*Disease resistance.*—Somewhat susceptible to mildew, bald spot and resistant as other carnations to diseases in general.

Wood (new): Bark—smooth.

Wood (old):

*Color.*—7.5YR 4/5.
*Bark.*—Slightly rough.

I claim:

The new and distinct variety of carnation plant substantially as herein disclosed, characterized as to novelty by the very white to very lightly shaded brilliant greenish yellow color of its blooms, the more serrated, feathery form of its blooms, well placed on long graceful stems, the strong fragrance of the blooms, and very vigorous, tall plant form.

No references cited.